US009861795B2

(12) United States Patent
Simmons et al.

(10) Patent No.: US 9,861,795 B2
(45) Date of Patent: Jan. 9, 2018

(54) DOUBLE BALLOON CATHETER

(71) Applicant: MUSC FOUNDATION FOR RESEARCH DEVELOPMENT, Charleston, SC (US)

(72) Inventors: Cephus Simmons, Mount Pleasant, SC (US); Rebecca Copenhaver DeLegge, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 566 days.

(21) Appl. No.: 14/365,269

(22) PCT Filed: Dec. 14, 2012

(86) PCT No.: PCT/US2012/069844
§ 371 (c)(1),
(2) Date: Jun. 13, 2014

(87) PCT Pub. No.: WO2013/090778
PCT Pub. Date: Jun. 20, 2013

(65) Prior Publication Data
US 2014/0336574 A1 Nov. 13, 2014

Related U.S. Application Data

(60) Provisional application No. 61/576,665, filed on Dec. 16, 2011.

(51) Int. Cl.
*A61M 25/10* (2013.01)
*A61M 3/02* (2006.01)
*A61B 10/02* (2006.01)

(52) U.S. Cl.
CPC ...... *A61M 25/1011* (2013.01); *A61M 3/0295* (2013.01); *A61B 10/02* (2013.01); *A61M 2025/1052* (2013.01); *A61M 2025/1093* (2013.01); *A61M 2210/1067* (2013.01)

(58) Field of Classification Search
CPC ...... A61B 17/12136; A61B 2017/3486; A61B 17/1204; A61M 25/10; A61M 29/02; A61M 31/00
See application file for complete search history.

(56) References Cited

U.S. PATENT DOCUMENTS

| 724,913 | A | * | 4/1903 | Montgomery | 604/278 |
| 2,687,131 | A | * | 8/1954 | Raiche | 604/101.05 |
| 2,693,191 | A | * | 11/1954 | Raiche | 604/101.05 |

(Continued)

FOREIGN PATENT DOCUMENTS

KR WO 0226293 A1 * 4/2002 ........... A61F 2/0009

OTHER PUBLICATIONS

International Preliminary Report on Patentability and Written Opinion in corresponding International Application No. PCT/US2012/069844, dated Jun. 17, 2014, 8 pages.

(Continued)

*Primary Examiner* — Scott Medway
(74) *Attorney, Agent, or Firm* — Meunier Carlin & Curfman LLC

(57) ABSTRACT

A catheter including a plurality of balloons extending from the outer surface of the catheter that when inflated create a seal between the catheter and the patient's thereby eliminating leakage of fluids from around catheter during the procedure.

29 Claims, 5 Drawing Sheets

(56) References Cited

U.S. PATENT DOCUMENTS

| | | | | |
|---|---|---|---|---|
| 2,936,760 A * | 5/1960 | Gants | | 604/101.03 |
| 3,154,077 A * | 10/1964 | Cannon | | 606/192 |
| 3,459,175 A * | 8/1969 | Miller | | 600/431 |
| 3,721,229 A * | 3/1973 | Panzer | | 600/435 |
| 3,765,413 A * | 10/1973 | Lepar | | 604/176 |
| 3,848,602 A * | 11/1974 | Gutnick | | 606/193 |
| 3,889,676 A * | 6/1975 | Greene | | 604/101.05 |
| 4,019,515 A * | 4/1977 | Kornblum et al. | | 604/101.05 |
| 4,555,242 A * | 11/1985 | Saudagar | | 604/103.08 |
| 4,686,985 A * | 8/1987 | Lottick | | 606/192 |
| 4,772,260 A * | 9/1988 | Heyden | | 604/45 |
| 4,893,623 A * | 1/1990 | Rosenbluth | | A61F 2/91 |
| | | | | 604/104 |
| 5,312,343 A * | 5/1994 | Krog et al. | | 604/101.03 |
| 5,496,271 A * | 3/1996 | Burton et al. | | 607/27 |
| 5,527,336 A * | 6/1996 | Rosenbluth | | A61F 2/958 |
| | | | | 600/116 |
| 5,624,395 A * | 4/1997 | Mikhail et al. | | 604/99.04 |
| 6,706,026 B1 * | 3/2004 | Goldstein et al. | | 604/278 |
| 6,716,252 B2 * | 4/2004 | Lazarovitz et al. | | 623/23.66 |
| 7,022,103 B2 * | 4/2006 | Cappiello et al. | | 604/102.01 |
| 7,360,544 B2 * | 4/2008 | Levien | | 128/897 |
| 8,439,819 B2 * | 5/2013 | Shalon et al. | | 600/32 |
| 8,939,932 B2 * | 1/2015 | McCloskey et al. | | 604/103.03 |
| 2002/0082610 A1 * | 6/2002 | Cioanta et al. | | 606/108 |
| 2002/0165521 A1 * | 11/2002 | Cioanta et al. | | 604/509 |
| 2007/0213661 A1 * | 9/2007 | Gobel | | 604/96.01 |
| 2012/0296272 A1 * | 11/2012 | Bidault et al. | | 604/101.05 |

OTHER PUBLICATIONS

Beets-Tan et al. "Measurement of Anal Sphincter Muscles: Endoanal US, Endoanal MR Imaging, or Phased-Array MR Imaging? A Study with Healthy Volunteers", Radiology 2001; 220:81-89.

\* cited by examiner

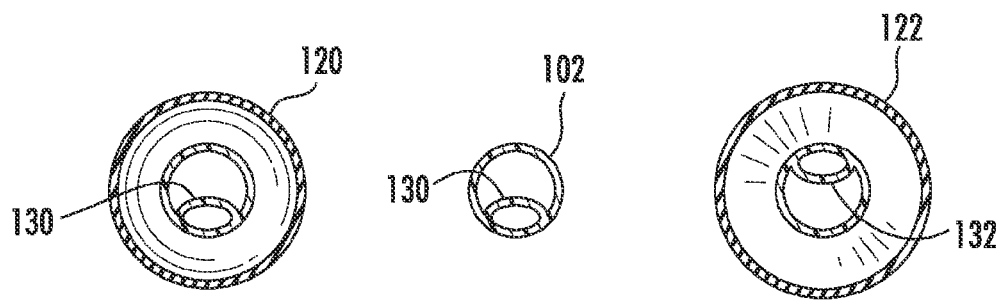
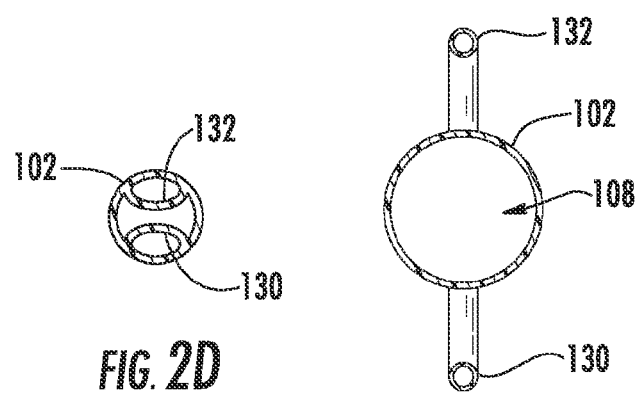

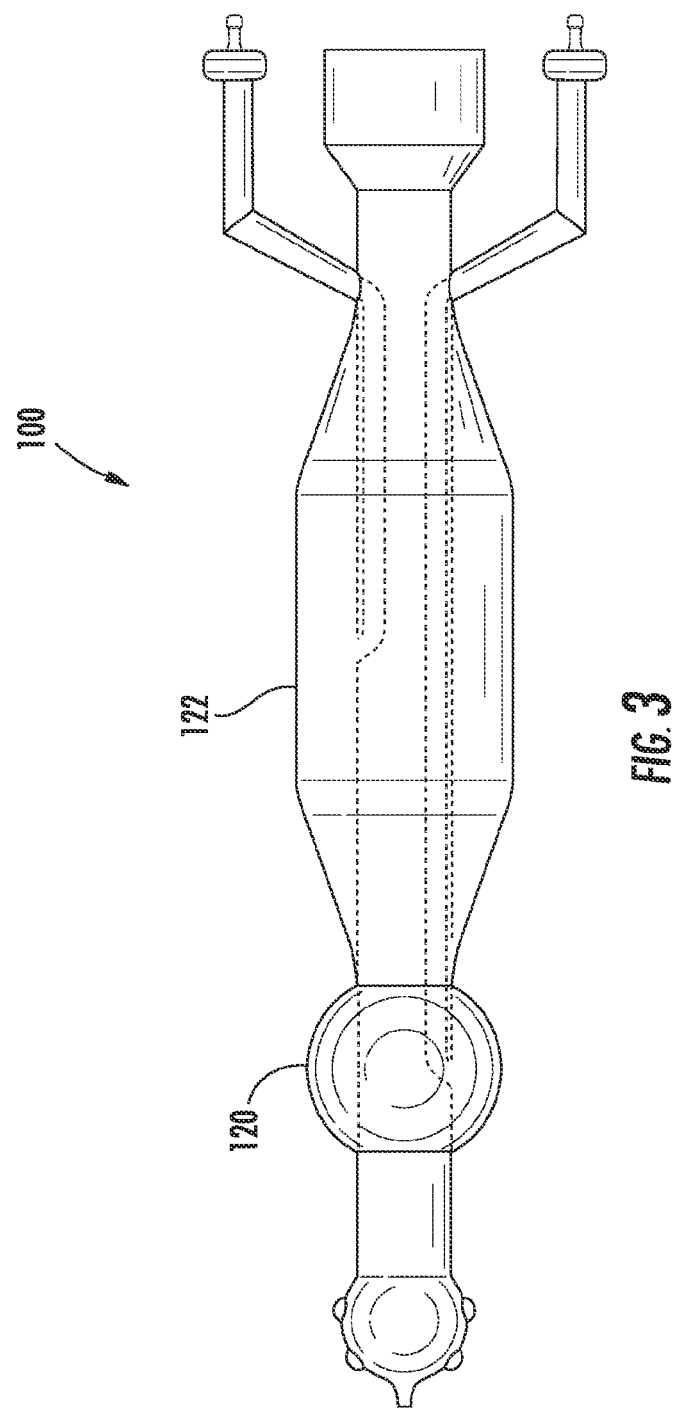

DOUBLE BALLOON CATHETER

CROSS-REFERENCE TO RELATED APPLICATIONS

This application claims priority to U.S. Provisional Application No. 61/576,665, filed Dec. 16, 2011, which is herein incorporated in its entirety by reference.

TECHNICAL FIELD

This invention relates to an apparatus and method providing a seal between a catheter and a body orifice.

BACKGROUND

Certain diagnostic and therapeutic procedures require access to an internal portion of a patient's body using a catheter. Catheters have been used in cardiovascular, urological, gastrointestinal, neurovascular and ophthalmic applications. Example gastrointestinal uses of catheters include the treatment of intussusceptions, inversion of one portion of the intestine within another. Intussusception is the most common cause of intestinal obstruction in children and occurs when the bowel telescopes into itself. It is the main cause of intestinal obstruction in infants with 80% to 90% of the events occurring in children ages three months to three years.

While the cause of intussusception is unknown, there are theories of why it occurs. Most patients are diagnosed with intussusception after they have had a bout of gastroenteritis, also known as stomach flu. Gastrointestinal infections can cause swelling of the lymph tissue that lines the intestinal wall, which can pull one part of the intestine into the other. Blood flow through the intestine is decreased thereby causing swelling and inflammation. The condition can progress from intestinal obstruction to necrosis of a segment of the intestine. The swelling can lead to perforation and generalized abdominal infection. Shock and dehydration can occur rapidly.

While surgery is the main treatment method for intussusception, barium or air enema reduction can be used as a less invasive treatment procedure. In general, the air procedure tends to be more efficient and quicker than using barium. During the air enema procedure, a catheter is placed in the patient's rectum. Once the catheter is in place, a seal must be created to substantially stop the leakage of air out of the rectum. The external portion of the catheter is attached to a pneumatic device which allows pressure regulation during the procedure. During treatment, as air and pressure within the bowel increase, the intussusception is reduced. Once reduced, the catheter is removed.

In order to achieve optimal results, a seal between the catheter and the rectum must be achieved to prevent leakage of airflow around the catheter. In most procedures it is very difficult, if not impossible, to achieve a complete seal. Current techniques to achieve a seal include holding or taping the buttocks together in an effort to compress the rectum and the fleshy buttocks to prevent air leakage. These methods are not only painful to the patient, but they can also be insufficient to achieve the desired seal. Failure to accomplish an effective seal will not only compromise the outcome of the procedure but will increase the procedure time and result in suboptimal outcome. In some cases, this suboptimal outcome requires surgery to correct the problem.

Accordingly, there remains a need in the art to provide safe and effective apparatus that maintains a seal between a catheter and a body orifice that can be used, for example, during non-surgical methods of treating intussusceptions using either air or barium enema reduction techniques.

SUMMARY

Presented are systems and methods to seal a catheter to a body orifice. An aspect of the present disclosure is directed a catheter comprising an elongated cannula, a first balloon and a second balloon. The elongated cannula can have a distal end, a proximal end and a central lumen extending there through. The first balloon can be configured to extend from an outer surface of the elongated cannula. The second balloon can also be configured to extend from the outer surface of the elongated cannula. The second balloon can be located on the outer surface of the elongated cannula between the first balloon and the distal end. The second balloon, when inflated, tapers from the outer surface of the elongated cannula towards the distal end of the elongated cannula. Inflation of the first balloon and the second balloon can create a seal between an internal portion of a person and an external portion of the person.

Another aspect of the present disclosure is directed to a colorectal sealing device. The sealing device can include a tubular body, a first balloon and a second balloon. The tubular body can be sized and configured to be inserted into a body of a person. The tubular body can include a distal end, a proximal end and a central lumen. The distal end can be located outside the body when at least a portion of the tubular body is inserted into the body. The proximal end can be located within the body of the person when at least a portion of the tubular body is inserted into the body. The central lumen can extend between the distal end and the proximal end and provide an access port for a surgical instrument. The first balloon can be located on a surface of the tubular body and have a first diameter at a deflated state and a second diameter at an inflated state. The second balloon can be located on the surface of the tubular body at a location between the first balloon and the distal end. The second balloon can have a first diameter at a deflated state and a second diameter at an inflated state. The second balloon, when at the inflated state, can taper from the surface of the tubular body towards the distal end of the tubular body. Inflation of the first balloon and the second balloon can create a seal between an internal portion of the body of the person and an external portion of the body of the person.

A further aspect of the present disclosure is directed to a method of creating a seal between an internal portion of a body of a person and an external portion of the body of the person. The method may include inserting an elongated cannula into the internal portion of the body of the person. The elongated cannula can include a first balloon configured to extend from a surface of the elongated cannula when inflated, the first balloon being inserted into the body in a deflated state. The elongated cannula can also include a second balloon configured to extend from the surface of the elongated cannula when inflated, the second balloon being inserted into the body in a deflated state. When inflated, the second balloon can taper from the surface of the elongated cannula towards the external portion of the body of the person. The method may further include inflating the first balloon and inflating the second balloon.

Another aspect of the present disclosure is directed to a catheter comprising an elongated cannula, a first balloon and a second balloon. The elongated cannula can have a distal end, a proximal end, and a central lumen extending there through. The first balloon can be configured to extend from an outer surface of the elongated cannula. The second balloon can be configured to extend from the outer surface of the elongated cannula. The second balloon can be located between the first balloon and the distal end. The second balloon can include a tapering surface that, when inflated, has a axial length greater than an axial length of a sphincter of a person.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

FIG. 2A is a cross-section view of an example catheter;
FIG. 2B is a cross-section view of an example catheter;
FIG. 2C is a cross-section view of an example catheter;
FIG. 2D is a cross-section view of an example catheter;
FIG. 2E is a cross-section view of an example catheter;
FIG. 3 is a top view of an example catheter.

DETAILED DESCRIPTION

Figure 1:
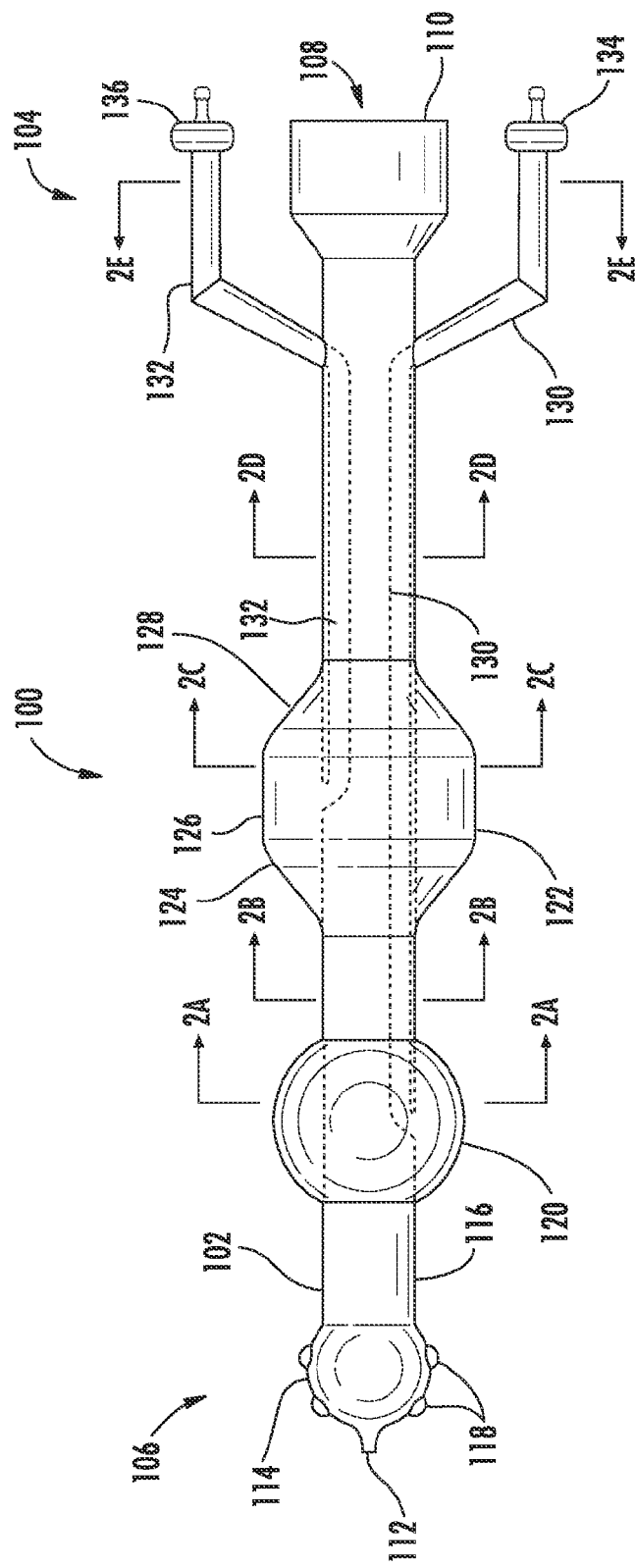
FIG. 1 is a top view of an example catheter.

Certain examples of the invention will now be described with reference to the drawings. In general, such embodiments relate to systems and methods to seal a catheter at a body orifice in order to substantially reduce or eliminate leakage of fluids or air between the orifice and the catheter during the procedure. The catheter can include a plurality of balloons extending from the outer surface of the catheter that when inflated create a seal between the catheter and the body orifice. FIG. 1 is a perspective view of an example catheter 100. The catheter 100 can include a slender flexible or inflexible tube composed of biocompatible material. For example, the catheter 100 can be composed of latex, urethane, silicone, thermoplastic elastomers, latex free or silicone coated material. The catheter 100 can be disposable or sterilized for repeated use.

The catheter 100 can include an access port and/or fittings and connections for completing diagnostics, to provide treatment and/or perform surgical procedures. For example, the catheter 100 can be used to take measurements and/or tissue samples, monitor an internal body condition, administration of fluids or gases (therapies, irritants, and gases, etc.), and allow drainage or otherwise remove matter from the body of the patient.

As illustrated in FIG. 1, the catheter 100 can include an elongated cannula 102 having a distal end 104 and a proximal end 106. The catheter 100 can include a central lumen 108 extending within the elongated cannula 102 between the distal end 104 and the proximal end 106. The central lumen 108 can extend between an opening 110 at the distal end 104 and an opening 112 at the proximal end 106. In an example catheter 100, the opening 112 can be sealed and/or blocked there by preventing access from central lumen 108 to the exterior of the catheter 100 at the opening 112. FIG. 2B provides a cross-section view of the elongated cannula 102 at section line 2B-2B. The proximal end 106 of the catheter 100 can include a tip 114. The tip 114 can define any suitable shape including, for example, round, elliptical, square, rectangular, or any other regular or irregular shape. As illustrated in FIG. 1, an example tip 114 can define a semi-circular profile. An example tip 114 can define a radius that extends beyond the outer surface 116 of the elongated cannula 102. For example, the tip 114 can define a semi-circular profile having radius of about 0.5 cm to 1 cm measured from the centerline of the elongated cannula 102. An example tip 114 can have a length of about 2 cm to 3 cm between the end surface of the elongated cannula 102 at the proximal end 106 and the location where the profile of the tip 114 joins the outer surface 116 of the elongated cannula 102. In an alternate example (not shown), the tip 114 can define a profile and/or contour corresponding to the profile of the outer surface 116.

In addition, or in the alternative to opening 112, the proximal end 106 can include secondary openings 118 located around on the surface of the tip 114. The size, shape, number, and location of the opening 112 and secondary openings 118 can vary depending on intended use of the catheter 100. As illustrated in FIG. 1, an example catheter 100 can include one end opening 112 and four secondary openings 118. In an example catheter 100, the opening 112 and the secondary openings 118 can include circular-shaped openings that vary in size from about 2 mm to 3 mm.

The catheter 100 can include a first balloon 120 located along the outer surface 116 of the elongated cannula 102. FIG. 2A provides a cross-section view of the first balloon 120 at section line 2A-2A. The first balloon 120 can be sized and configured to extend radially from the outer surface 116 of the elongated cannula 102. The first balloon 120 can be composed of the same or different material as the elongated cannula 102. The first balloon 120 can also be composed of a complaint or non-compliant material. The first balloon 120 can be composed of a flexible or semi-flexible material. Inflation of the first balloon 120 can provide an anchor for the catheter 100 within the body of the patient. Therefore, the size and shape of the inflated first balloon 120, with respect to physical dimensions and/or volume, can vary in size depending on the intended use of the catheter 100. The longitudinal and/or axial profile defined by the outer perimeter of the first balloon 120 can define any suitable shape including, for example, circular, elliptical, square, rectangular, or any other regular or irregular shape. For example, as illustrated in FIG. 1, the longitudinal profile defined by the outer perimeter of the first balloon 120 can have a partial circle or round shape. Likewise, as illustrated in FIG. 2A, the axial profile defined by the outer perimeter of the first balloon 120 can define a circular or round shape. It is also contemplated that the size of the first balloon 120 will vary depending on the patient's anatomy. For example, when the catheter 100 is a colorectal catheter used, for example, to treat intussusceptions, inflation of the first balloon 120 can anchor the catheter 100 within the patient's rectum. That is, the diameter of the inflated first balloon 120 is equal to or greater than the diameter of the portion of the rectum where the catheter 100 is located. An example, the inflated first balloon 120 can have a diameter of about 2 cm to 4 cm and a length of about 1.5 cm to 2.5 cm. The first balloon 120 can have a capacity of 20 cc to 50 cc depending on the compliance of the material of the first balloon 120.

Similarly, the location of the first balloon 120 with respect to the proximal end 106 along the body of the elongated cannula 102 can vary depending on the intended use of the catheter 100. As illustrated in FIG. 1, in an example catheter 100, the first balloon 120 is spaced apart from the proximal end 106 and/or tip 114. For example, the first balloon 120 can be located 2 cm to 4 cm from tip 114 (measured from where the tip 114 joins the outer surface 116). In another example, the first balloon 120 can be located adjacent to the tip 114. In another example, the first balloon 120 can be located adjacent to the most distal side hole 118. In a further example, the first balloon 120 can be located on the proximal end ## of the catheter 100, eliminating the tip 114 and any of the secondary openings 118, such that the opening 112 and the central lumen 108 provide access to the internal portion of the patient's body.

The cannula can also include a second balloon 122 located along the outer surface 116 of the elongated cannula 102. FIG. 2C provides a cross-section view of the second balloon 122 at section line 2C-2C. The second balloon 122 can be located between the first balloon 120 and the distal end 104. As illustrated in FIG. 1, the second balloon 122 can be located at a distance from the first balloon 120. In an alternate embodiment, illustrated in FIG. 3, the second balloon 122 can abut or otherwise be adjacent to the first balloon 120. The distance between the second balloon 122 and the distal end 104 can vary in relation to the total catheter length. The second balloon 122 can be sized and configured to extend radially from the outer surface 116 of the elongated cannula 102. The second balloon 122 can be composed of the same or different material as the elongated cannula 102 and/or the first balloon 120. The second balloon 122 can be composed of a flexible or semi-flexible, compliant or non-compliant material.

Figure 4:
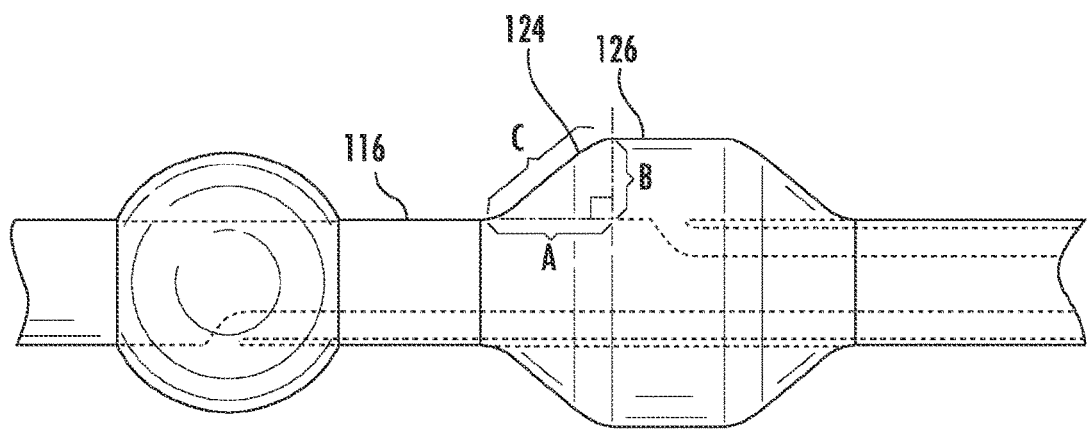
FIG. 4 is a partial top view of an example catheter.

The size and shape of the inflated second balloon 122 (dimensions and/or volume) can vary depending on the intended use and size of the catheter 100. The longitudinal and/or axial profile defined by the outer perimeter of the second balloon 122 can define any suitable shape including, for example, circular, elliptical, square, rectangular, or any other regular or irregular shape. As illustrated in FIG. 1, the longitudinal profile defined by the outer perimeter of the second balloon 122 includes a first taper 124, an inflated outer surface 126, and a optional second taper 128. The longitudinal profile defined by the first taper 128 can extend in a direction along a longitudinal axis of the elongated cannula 102 from the outer surface 116 to an inflated outer surface 126 of the inflated second balloon 122. As illustrated in FIG. 4, the first taper 124 can optionally include a base or "run" designated by the reference symbol "A." The run extends in the direction of the longitudinal axis of the elongated cannula 102 from the outer surface 116 and defines the axial length of the first taper 124. The first taper 124 can include a height or "rise" designated by the reference symbol "B". The rise extends at a 90° angle from the run and terminates at the inflated outer surface 126. The taper also includes a hypotenuse-length designated by the reference symbol "C" and defined by the hypotenuse of the triangle created by rise and the run.

The first taper 124 can be gradual over the length of the elongated cannula 102 or it may be aggressive (i.e., have a steeper slope) as determined by the patient's anatomy. For example, a thicker and longer sphincter muscle (e.g., anal sphincter muscle) may require a longer less aggressive taper than a thinner shorter sphincter muscle (e.g., biliary sphincter). In the case of the biliary sphincter, for example, the sphincter muscle is axially short and thinner (i.e., does not extend deeply into the surrounding tissues), therefore, a more aggressive (steep) taper can be used. As illustrated in Table 1 below, the slope of the first taper 124 when the catheter 100 is used with the biliary sphincter can be about 33%. In another example, an obese patient may have a thicker and longer sphincter muscle when compared to a similar non-obese patient. Therefore, when used on an obese patient, the first taper 124 may be more aggressive (steep) than the first taper 124 used on a non-obese patient for the same procedure.

In some cases, including the rectum, the sphincter and surround tissues (e.g., buttocks) can be considered when designing the second balloon 122 and the first taper 124. For example, in a patient having excess body tissue (e.g., an obese patient), the buttocks can be considered as part of the tissue compressed between the first balloon 120 and the second balloon 122. The second balloon 122 can also include a second taper 128 similar in form and structure to the first taper 124. The second taper 128 can extend from the inflated outer surface 126 to the outer surface 116 in a direction towards the distal end 104. In an alternate embodiment (not shown), the second balloon 122 does not include the second taper 128. Instead, the longitudinal profile defined by the outer perimeter of the distal end of the second balloon 122 can include various other shapes and configurations such as, for example, rounded, square, or include any other edge formation known in the art.

As illustrated in FIG. 2C, the axial profile defined by the outer perimeter of the inflated outer surface 126 can define a circular or round shape. In an example catheter 100, the axial profile of the outer perimeter of the inflated outer surface 126 can define the maximum diameter of the second balloon 122, when inflated. In the example catheter 100 shown in FIG. 1, the maximum axial diameter defined by the second balloon 122 is greater than the maximum axial diameter defined by the first balloon 120. In an alternative embodiment (not shown), the maximum axial diameter defined by the second balloon 122 is equal to or less than the maximum axial diameter defined by the first balloon 120.

Inflation of the first balloon 120 and the second balloon 122 creates a seal at the catheter 100 between an internal portion of the patient and the body orifice (external). This seal is created by compressing internal body tissue between the first balloon 120 and the second balloon 122. The seal can also be created by the "sliding" motion of the internal body tissue towards the first balloon 120 created by the inflation of the second balloon 122.

The catheter 100 can be sized and configured to be inserted into a body cavity, duct, or vessel of the patient. In particular, the catheter 100 can be sized and configured to be inserted into internal body tissue including a sphincter muscle. An example catheter 100 can be configured for use at sphincter muscles associated with a natural or created valved lumen or cavity within the patient including, for example, cardiovascular, urological, gastrointestinal and various percutaneous applications. The human body includes over 50 sphincter muscles. The catheter 100 can be used, for example, with the following sphincter muscles: sphincter pupillae or pupillary sphincter, belonging to the iris in the eye; orbicularis oris muscle around the mouth; cardia/lower esophageal sphincter or cardiac sphincter at the upper portion of the stomach which prevents the acidic contents of the stomach from moving into the esophagus; pyloric sphincter at the lower end of the stomach; sphincter of Oddi, or Glisson's sphincter, controlling secretions from the liver, pancreas and gall bladder into the duodenum; urethral sphincter (internal and external), controlling the exit of urine from the body; and anus (internal and external). An appropriate catheter 100 length and size can be selected from those included in the following ranges, or from other sizes based on a variety of medical/surgical considerations. For example, a surgeon or other medical professional can determine an appropriate catheter 100 length and size by evaluating the medical situation in which the device will be used. For example, the catheter 100 can be used for gastro-intestinal procedures, such as, identification and treatment of colon polyps, diverticulitis, diverticulosis, Crohn's disease, inflammatory bowel disease (IBD), ulcerative colitis (UC), and colon carcinoma. The catheter 100 optimally ranges ranging in length from 30 cm to 60 cm. The catheter 100 can also range in size from 8 F to 28 F, with sizes 14 F to 24 F being used on adults and 8 F to 12 F being used on children.

Figure 5:
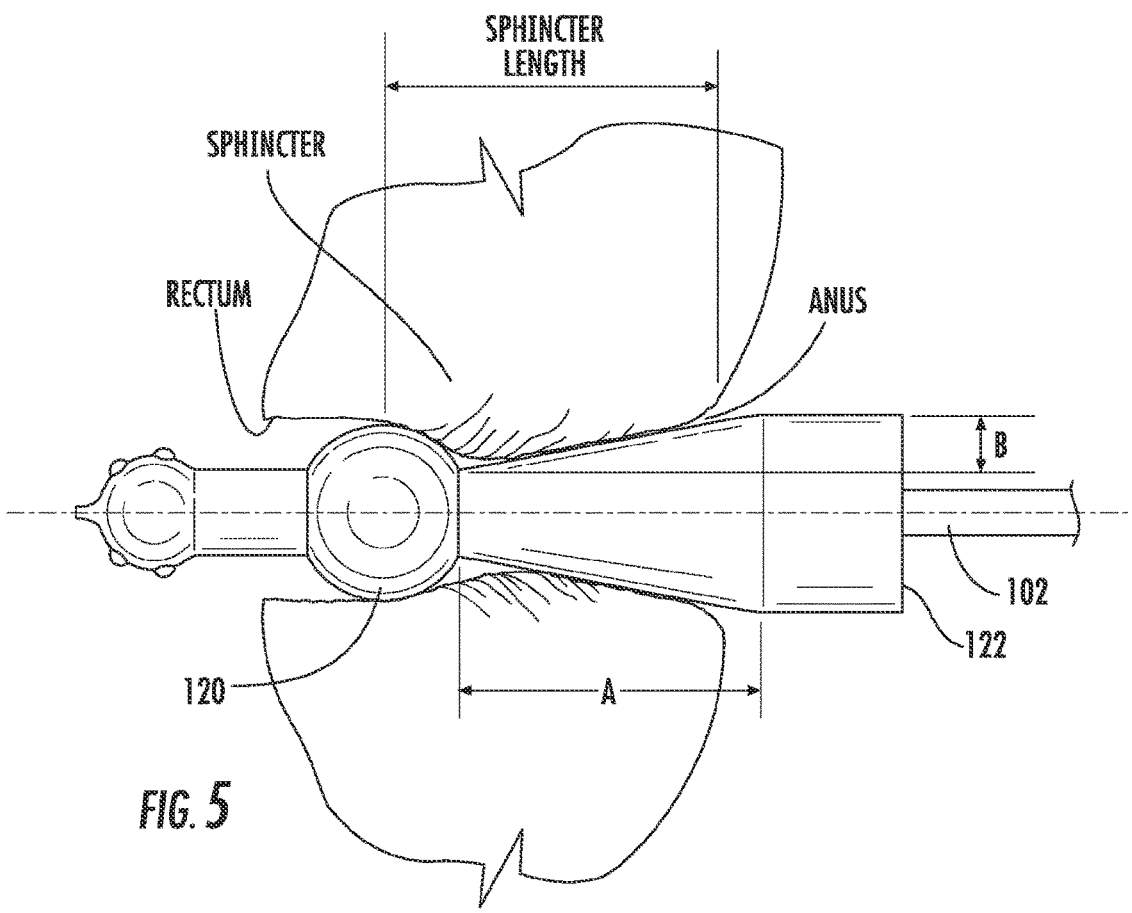
FIG. 5 is a schematic diagram of an example catheter positioned within a patient.
Figure 5A:
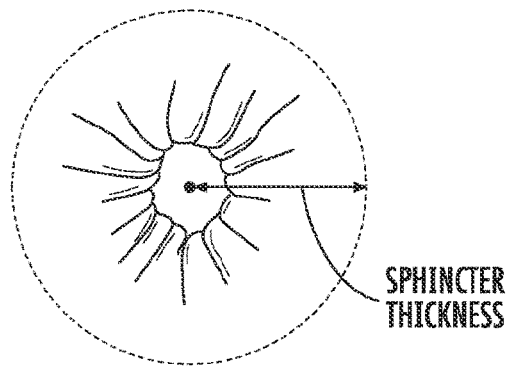
FIG. 5A is a schematic diagram of a sphincter of a patient.

FIG. 5 provides a schematic diagram of the catheter 100 positioned within an example patient. The example catheter 100 includes a second balloon 122 positioned adjacent to the first balloon 120. This seal can be created by compressing the sphincter muscle between the first balloon 120 and the second balloon 122. For example, as the second balloon 122 is inflated, the sphincter muscle is compressed/pushed in the direction towards the first balloon 120 and a seal is created. The axial diameter of the elongated cannula 102 is less than the diameter of the sphincter. When inserted, the first balloon 120 is located inside the rectum. The second balloon 122 is positioned along the sphincter muscle. As the second balloon 122 is inflated, the sphincter is compressed between the balloons and a seal is created.

In an example catheter 100, the length and thickness of the sphincter muscle correlate to the run and rise of the first taper 124. Table 1 provides example correlations between the length and thickness of various sphincter muscles contemplated for use with the present system and example run and rise values for the first taper 124.

TABLE 1

Sphincter and Taper Comparison

| Sphincter | Axial Length of Sphincter (mm) | Thickness of Sphincter (mm) | Run of First Taper (mm) | Rise of First Taper (mm) | Slope of First Taper |
|---|---|---|---|---|---|
| Anal | 80-100 | 2-6 | 92 | 10 | 10/92 = 10% |
| Pyloric | 80 | 10 | 100 | 20 | 20/100 = 20% |
| Urinary | 20-100 | 14 | 120 | 30 | 30/120 = 25% |
| Biliary | 20 | 5 | 30 | 10 | 10/30 = 33% |

As demonstrated in Table 1, the longer the sphincter the longer the run of taper 124 is required. In an example catheter 100, the run of the first taper 124 is greater than the length of the sphincter muscle along the longitudinal axis of the catheter 100. Example sphincter muscle lengths can range between about 2 cm and 10 cm, including, for example, 2 cm, 7.2 cm, 8 cm, and 10 cm. Example taper run lengths can be greater than about 2 cm, including, for example, 2 cm, 3 cm, 5, cm, 9 cm, 10 cm, and 12 cm. For example, when the catheter 100 is a colorectal catheter and the length of the anal sphincter is about 7.2 cm, the run of the corresponding first taper 124 can be about 9.2 cm. In a further example, the catheter 100 is a pyloric catheter. The length of the pyloric sphincter is about 8 cm, the run of the corresponding first taper 124 is about 10 cm.

As similarly demonstrated in Table 1, the thicker the sphincter muscle the greater the rise of taper 124 is required. In an example catheter 100, the rise of the first taper 124 is greater than the thickness of the sphincter muscle in a direction perpendicular to the longitudinal axis of the catheter 100. For example, when the catheter 100 is a colorectal catheter and the thickness of the anal sphincter is about 2 cm to 6 cm, the rise of the corresponding first taper 124 can be about 10 cm. It is also contemplated that an effective seal can be achieved when the rise of the first taper 124 is equal to or less than the thickness of the sphincter muscle.

In a further example catheter 100, the distance between the first balloon 120 and the second balloon 122 is less than the length of the sphincter muscle such that at least a portion of the first taper 124 is located adjacent to the sphincter muscle. For example, when the catheter 100 is a colorectal catheter and the length of the anal sphincter is about 7.2 cm, the distance between the first balloon 120 and the second balloon 122 can be about 2 cm to 8 cm.

As outlined above, the central lumen 108 of the elongated cannula 102 terminates at the distal end 104 at opening 110. The opening 110 can have a diameter larger than the diameter of the elongated cannula 102. In an alternate embodiment (not shown), the opening 110 can have a diameter less than or equal to the diameter of the elongated cannula 102. In an example catheter 100, opening 110 can have a diameter of about 0.8 cm. The opening can include a taper extending from the outer surface 116 to the diameter of the opening 110. An example opening 110 can include a syringe-type opening configured for the introduction of fluid or air into the patient's body.

The catheter 100 can also include a first lumen 130 and a second lumen 132 extending within the central lumen 108. FIG. 2D provides a cross-section view of the elongated cannula 102 including the first lumen 130 and the second lumen 132 at section line 2D-2D. The first lumen 130 can be in fluid communication with the first balloon 120. Using the first lumen 130, the user can provide a fluid (gas and/or liquid) to inflate/deflate the first balloon 120. Likewise, the second lumen 132 can be in fluid communication with the second balloon 122. Using the second lumen 132, the user can provide a fluid (gas and/or liquid) to inflate/deflate the second balloon 122. In an alternate embodiment, the first lumen 130 and/or the second lumen 132 are located outside the central lumen 108 of the catheter 100. For example, the first lumen 130 and/or the second lumen 132 can extend along the outer surface 116 of the elongated cannula 102.

The first lumen 130 can extend through the outer surface 116 of the elongated cannula 102 to an input 134 at the distal end 104 of the catheter 100. Similarly, the second lumen 132 can extend through the outer surface 116 of the elongated cannula 102 to an input 136 at the distal end of the catheter 100. FIG. 2E provides a cross-section view of the elongated cannula 102/opening 110, input 134 and input 136 at section line 2E-2E. The inputs 134 and 136 can include a syringe-type opening similar to opening 110. In another example, the inputs 134 and 136 can include a luer-lock syringe connection. In a further example, the inputs 134 and 136 and/or first lumen 130 and second lumen 132 can include a one-way valve member. In an example catheter 100, the length of the catheter between the distal end 104 and where the first lumen 130 and the second lumen 132 extend through the outer surface 116 can vary in relation to the total length of the catheter 100. In an example catheter 100, the distance can be about 4 cm to 6 cm. Likewise, the length of the first lumen 130 and the second lumen 132 extending outside the outer surface 116 can vary. In an example catheter 100, the distance can be about 4.5 cm to 6.5 cm. The shape of the first lumen 130 and the second lumen 132 extending outside the outer surface 116 can be curved, angle, straight, or take any other direction/shape.

In operation, the catheter 100 can optionally be used for intussusception reduction, barium or water soluble enema, fistulogram, virtual colonoscopy and other procedures requiring an effective seal between the catheter 100 and the patient. The catheter 100 can be used by inserting the proximal end 106 of the elongated cannula 102 into the body of the patient. The catheter 100 can be inserted at either a natural or created orifice in the patient's body. Natural orifices include, for example, the anus, pylorus, urethra and biliary tract. The user can also create an orifice in the patient's body, for example, a surgical opening. A portion of the elongated cannula 102 can be inserted such that the proximal end 106 is located within the patient and the distal end 104 is located outside the patient's body. In an example, the inserted portion includes the first balloon 120 and a portion of the second balloon 122. For example, as illustrated in FIG. 5, the first balloon 120 can be inserted within the patient past the sphincter muscle and at least a portion of the second balloon 122 can be inserted within the patent.

At insertion, the first balloon 120 and the second balloon 122 are in a deflated state. In the deflated state, the first balloon 120 and the second balloon 122 may have a diameter corresponding to the diameter of the elongated cannula 102. In a further example, in the deflated state, the first balloon 120 and the second balloon 122 may have a diameter greater than the diameter of the elongated cannula 102 but less than the diameter of the orifice in the body of the patient. For example, the deflated balloons and the elongated cannula 102 may have a diameter less than the diameter defined by the sphincter muscle corresponding to the orifice.

Upon insertion, internal tissue (i.e., the sphincter muscle) is located along the second balloon 122. For example, upon insertion, the sphincter muscle associated with the orifice is located along at least a portion of the second balloon 122. In an example method, all or a significant portion of the length sphincter muscle is located along first taper 124 of the second balloon 122.

Once the catheter 100 is properly located, the first balloon 120 is inflated. The first balloon 120 can be inflated at least partially or to capacity. In an example method, the first balloon 120 is inflated to its maximum intra-body capacity. Once inflated, the first balloon 120 anchors the elongated cannula 102 within the patient's body.

The second balloon 122 is then inflated. The second balloon 122 can be inflated at least partially or to capacity. In an example method, the second balloon 122 is inflated to its maximum intra-body capacity. The second balloon 122 can be rapidly inflated. In another example, the second balloon 122 is slowly/steadily inflated to until an effective seal is achieved. By inflating the second balloon 122 slowly/steadily, the second balloon 122 can align with the first balloon 120 to prevent motion of the catheter 100 in the longitudinal direction.

The first balloon 120 can be inflated first, independently of the second balloon 122. In an alternate method, when inflation of the second balloon 122 is initiated, the first balloon 120 is partially inflated. Inflation of the second balloon 122 can compress the internal body tissue (e.g., sphincter muscle) between the first balloon 120 and the second balloon 122. Inflation of the second balloon 122 can also result in the internal body tissue moving, sliding, or rolling from the area of the first taper 124 towards the first balloon 120. By inflating the second balloon 122, and pressing the internal body tissue between the first balloon 120 and the second balloon 122, a seal is created around the catheter 100 at the orifice thereby preventing leakage from around catheter 100.

In operation, the catheter 100 can also be used to provide improvement for CT (computed tomography) colonoscopy procedures. During the procedure, a catheter can be inserted into the rectum of the patient. Carbon dioxide is then insufflated into the colon. If the colon is not completely distended, the study is limited, that is not all areas of the colon are visible thus not giving complete information. Catheter 100 can be used to create the seal, thus reducing the possibility of carbon dioxide leak and improving the likelihood of a fully distended colon.

The catheter 100 may also be used to provide an enema to a patient, in particular, barium enemas. When performing an enema, liquids such as barium, are introduced into the colon. If the patient does not have good rectal tone, the barium will leak out. This prevents barium from reaching the necessary location along the colon and into the cecum. Use of the catheter 100 to create seal significantly reduces or prevents liquid barium from leaking out of the rectum.

During the procedure, the catheter 100 is connected to a tubing set with a stopcock. The stopcock is adjusted to close access to the tubing. The patient is placed on the treatment table in a left lateral position. The catheter tip 114 is lubricated using, for example, petroleum jelly. The catheter 100 is then inserted into the rectum until it is within the rectum and the patient's buttocks are taped together. The patient is placed in the supine position. Under fluoroscopy, the first balloon 120 is inflated by connecting a syringe filled with saline to the input 134. An insufflator with a gauge is connected to the catheter 100. The second balloon 122 is minimally inflated with a syringe filled with saline attached at input 136. The second balloon 122 is then filled to accomplish the desired seal. The stopcock is then adjusted to allow the flow of air into the rectum and under fluoroscopy guidance, colonic insufflations is initiated.

During insufflation, the user can continue to observe the pressure gauge to ensure the pressure remains in the allotted range for the procedure. A pressure release valve can be placed between the insufflator and the stopcock. The pressure valve will release pressure when the pressure reaches 120 mmHg. The intussusceptum is followed until it is reduced and air reflux into the small bowel through the ileo-cecal valve is achieved. The escape of air leaking out of the rectum around the catheter 100 can be observed by the user. A leak will decrease intra-colonic pressure, thereby minimizing the chance of a successful reduction. If a leak is found, the second balloon 122 can be further inflated until the leak is eliminated. The catheter 100 can be used to eliminate the peri-rectal air leakage, which in turn, will provide optimal intra-colonic pressure and the success rate for intussusception reduction increases exponentially when the optimal pressure is maintained. This, in turn, will decrease the length of the procedure and thereby decreasing the radiation dose to the patients and the medical personnel.

After the removal of the catheter 100 and the remaining intussusception tools, the patient may have a bowel movement. The patient is then cleaned up and removed from the fluoroscopy table. If there are questions/concerns with respect to the reduction of the intussusception, an ultrasound can be completed. In some cases, the radiologist may recommend the patient to have surgery for reduction secondary to the findings on the air enema procedure. In other cases, the reduction procedure can be repeated at a later time. When the patient returns for a subsequent procedure, all steps of the preparing and performing the procedures are the same.

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

In addition, the various examples disclosed herein may be adapted for use in virtually any interior body region where a seal around a catheter is required for a therapeutic or diagnostic purpose. It is also anticipated that certain examples could be used for purposes other than medical, such as construction, manufacturing, and excavation, among others; accordingly, nothing herein is intended to limit application of the various examples to purely medical uses.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

What is claimed is:

1. A catheter comprising:
   an elongated cannula having a distal end, a proximal end, and a central lumen extending there through;
   a first balloon configured to extend from an outer surface of the elongated cannula; and
   a second balloon configured to extend from the outer surface of the elongated cannula, the second balloon located on the outer surface of the elongated cannula between the first balloon and the distal end,
   wherein the second balloon, when inflated, includes a tapered portion having a continually increasing taper from a proximal end of the first balloon towards a distal end of the second balloon, the tapered portion extending within an internal portion of a person within a sphincter muscle when the second balloon is inflated, a portion of the second balloon extending past the sphincter muscle and external to the person when the second balloon is inflated; and
   wherein inflation of the first balloon and the second balloon creates a seal between the internal portion of the person and an external portion of the person.

2. The catheter of claim 1, wherein the seal is created by compressing a body tissue of the person between the first balloon and the second balloon.

3. The catheter of claim 2, wherein the internal portion of the person includes an anal canal and rectum and the body tissue comprises an anal sphincter muscle of a person,
   wherein a distance between the first balloon and the second balloon is less than a length of the sphincter muscle such that the tapered portion of the second balloon is located adjacent to the sphincter muscle.

4. The catheter of claim 1, wherein inflation of the first balloon provides an anchor for the catheter within the internal portion of the person,
   wherein inflation of the second balloon creates an airtight seal between the second balloon and an anal canal of the person.

5. The catheter of claim 1, wherein a longitudinal profile defined by an outer perimeter of the first balloon includes a partial-circular shape,
   wherein a longitudinal profile of the second balloon includes the tapered portion, an adjacent constant diameter portion, and a second tapered portion, the second tapered portion tapers from the constant diameter portion to the outer surface of the elongated cannula towards the proximal end of the elongated cannula,
   wherein a longitudinal profile defined by an outer perimeter of the second balloon includes a partial-conical shaped defined by the tapered portion, a cylindrical shape defined by the constant diameter portion, and an opposite second partial-conical shape defined by the second tapered portion.

6. The catheter of claim 3, wherein an axial length of the tapered portion in a direction along a longitudinal axis of the elongated cannula is greater than a length of the sphincter muscle along the longitudinal axis of the elongated cannula.

7. The catheter of claim 3, wherein the height of the tapered portion is defined by a perpendicular distance between an axial end of the tapered portion at the outer surface of the elongated cannula and an other axial end of the tapered portion at an outer surface of the second balloon when inflated,
   wherein the height of the tapered portion is greater than a thickness of the sphincter muscle in a direction perpendicular to the longitudinal axis of the elongated cannula.

8. The catheter of claim 1, wherein an axial diameter defined by the second balloon, when inflated, is greater than an axial diameter defined by the first balloon, when inflated.

9. The catheter of claim 1, further including:
   a first lumen extending within the central lumen in fluid communication with the first balloon; and
   a second lumen extending within the central lumen in fluid communication with the second balloon.

10. The catheter of claim 9,
    wherein the first lumen includes an input at the distal end, the input extending through the outer surface of the elongated cannula;
    wherein the second lumen includes an input at the distal end, the input extending through the outer surface of the elongated cannula.

11. A colorectal sealing device comprising:
    a tubular body sized and configured to be inserted into an anal canal and rectum of a body of a person, the tubular bodying including:
      a distal end located outside the body when at least a portion of the tubular body is inserted into the body;
      a proximal end located within the body of the person when at least a portion of the tubular body is inserted into the body; and
      a central lumen extending between the distal end and the proximal end providing an access port for a surgical instrument;
    a first balloon located on a surface of the tubular body and having a first diameter at a deflated state and a second diameter at an inflated state; and
    a second balloon located on the surface of the tubular body at a location between the first balloon and the distal end, the second balloon having a first diameter at a deflated state and a larger second diameter at an inflated state;

wherein the second balloon, when at the inflated state, includes a tapered portion having a continually increasing taper from a proximal end of the first balloon towards a distal end of the second balloon, a portion of the tapered portion located within the body of the person and adjacent a wall of the anal canal when the second balloon is inflated and an other portion of the tapered portion extending past the anal canal and external to the person when the second balloon is inflated; and wherein inflation of the first balloon and the second balloon creates a seal between an internal portion of the body of the person and an external portion of the body of the person.

12. The sealing device of claim 11, wherein the seal is created by compressing an anal sphincter muscle of the person between the first balloon and the second balloon, wherein inflation of the second balloon creates a seal between the anal canal and the tubular body.

13. A method of creating a seal between an internal portion of a body of a person and an external portion of the body of the person, the method comprising:

inserting an elongated cannula into the internal portion of the body of the person, the elongated cannula including:

a first balloon configured to extend from a surface of the elongated cannula when inflated, the first balloon inserted into the body in a deflated state;

a second balloon configured to extend from the surface of the elongated cannula when inflated, the second balloon located at least partially within the body of the person, the second balloon inserted into the body in a deflated state, the second balloon when inflated the second balloon includes a tapered portion having a continuously increasing taper from a proximal end of the first balloon towards a distal end of the second balloon that tapers from the surface of the elongated cannula towards the external portion of the body of the person;

inflating the first balloon; and inflating the second balloon such that the tapered portion extends within the anal canal of the person at a location within the anal sphincter muscle and a portion of the second balloon extending past the anal sphincter muscle and external to the person.

14. The method of claim 13, wherein the first balloon is at least partially inflated before the second balloon is inflated.

15. The method of claim 13, wherein the first balloon is fully inflated before the second balloon is inflated, wherein inflating the first balloon and the second balloon anchor the elongated cannula within the internal portion of the body of the person.

16. The method of claim 13, wherein inflating the second balloon compresses a body tissue of the person between the first balloon and the second balloon.

17. The method of claim 13, wherein the length of the tapered portion in a direction along a longitudinal axis of the elongated cannula is greater than a length of the anal sphincter muscle of the person along the longitudinal axis of the elongated cannula.

18. The method of claim 13, wherein the distance between the first balloon and the second balloon is less than a length of the anal sphincter muscle of the person.

19. The method of claim 13, wherein inserting the elongated cannula includes inserting the elongated cannula into at least one of a natural orifice in the body of the person and a created orifice in the body of the person.

20. The method of claim 19, wherein the natural orifice includes at least one of an anus, a pylorus, a urethra, a biliary tract, a valved lumen, and a surgically created cavity.

21. A catheter comprising:

an elongated cannula having a distal end, a proximal end, and a central lumen extending there through;

a first balloon configured to extend from an outer surface of the elongated cannula; and a second balloon configured to extend from the outer surface of the elongated cannula, the second balloon located between the first balloon and the distal end, the second balloon including a tapering surface when inflated such that the tapering surface has a continually increasing taper from a proximal end of the first balloon towards a distal end of the second balloon extends within a sphincter, wherein the tapering surface has an axial length greater than an axial length of a sphincter of a person and extends past the sphincter external to the person when the second balloon is inflated.

22. The catheter of claim 21, wherein inflation of the first balloon and the second balloon creates a seal between an internal portion of a person and an external portion of the person.

23. The catheter of claim 21, wherein the sphincter of the person includes at least one of the anal sphincter, the pyloric sphincter, the urinary sphincter, and the biliary sphincter.

24. The catheter of claim 21, wherein the axial length of the tapering surface is greater than about 2 cm.

25. The catheter of claim 21, wherein the axial length of the tapering surface ranges from about 3 cm to about 12 cm.

26. The catheter of claim 21, wherein the axial length of the tapering surface ranges from about 5 cm to about 12 cm.

27. The catheter of claim 21, wherein the axial length of the tapering surface ranges from about 9 cm to about 12 cm.

28. The catheter of claim 21, wherein the axial length of the tapering surface ranges from about 10 cm to about 12 cm.

29. The catheter of claim 3, wherein at least 50% of the length of the sphincter muscle is adjacent the tapered portion of the second balloon.

* * * * *